United States Patent
Haynes et al.

[11] Patent Number: 6,106,855
[45] Date of Patent: Aug. 22, 2000

[54] PROTEIN STABILIZED OIL-IN-WATER EMULSIONS

[75] Inventors: Carla A. Haynes, Cambuslang; Wilson Harvey, Gargunnock, both of United Kingdom

[73] Assignee: Johnson & Johnson Medical, Inc., Arlington, Tex.

[21] Appl. No.: 08/035,002

[22] Filed: Mar. 22, 1993

[30] Foreign Application Priority Data

Mar. 25, 1992 [GB] United Kingdom ............... 9206508

[51] Int. Cl.[7] ................................................ A61L 15/00
[52] U.S. Cl. ........................ 424/445; 424/444; 424/449
[58] Field of Search .................... 424/445, DIG. 13, 424/443; 514/938, 939, 944, 887, 801

[56] References Cited

U.S. PATENT DOCUMENTS

| | | | |
|---|---|---|---|
| 3,435,117 | 3/1969 | Nichols | 424/445 |
| 3,632,361 | 1/1972 | Battista | 106/122 |
| 3,823,212 | 7/1974 | Chvapil | 264/49 |
| 4,312,675 | 1/1982 | Pickens et al. | 106/171 |
| 4,412,947 | 11/1983 | Cioca | 260/123 |
| 4,571,422 | 2/1986 | Symes et al. | 536/114 |
| 4,670,550 | 6/1987 | Bleeker et al. | 536/114 |

FOREIGN PATENT DOCUMENTS

| | | |
|---|---|---|
| 0 532 119 A1 | 3/1993 | European Pat. Off. . |
| 6652 M | 12/1966 | France . |
| 55-84167 | 6/1980 | Japan . |
| 034923 | 12/1985 | Japan . |
| 2 058 084 | 9/1980 | United Kingdom . |

OTHER PUBLICATIONS

Collagen Sponge: Theory and Practice of Medical Applications; J. Biomed. Mater. Res., vol. 11, pp. 721–741 (1977), Milos Chvapil.

Collagen Biomaterials Characteristics and Applications; JALCA, vol. 80, pp. 195–212 (1985), Alain Huc.

Derwent WPI Abstract JP–A–55082621, Jun. 21., 1980.

Derwent WPI Abstract JP–B–85034923, Jun. 25, 1980.

Eaglstein et al. (1980). J. Inv. Dermatol. 74(2) : 90–91.

*Primary Examiner*—Thurman K. Page
*Assistant Examiner*—William E. Benston, Jr.
*Attorney, Agent, or Firm*—James Riesenfeld; Andrew C. Farmer; Theodore J. Shatynski

[57] ABSTRACT

Stable oil-in-water emulsions are prepared by mixing oil, water and an insoluble protein at high shear. By varying the amount of insoluble protein the emulsions may be made liquid, semisolid or solid. The preferred insoluble proteins are insoluble fibrous proteins such as collagen. The emulsions may be medicated with hydrophilic or hydrophobic pharmacologically active agents and are useful as or in wound dressings or ointments.

9 Claims, No Drawings

PROTEIN STABILIZED OIL-IN-WATER EMULSIONS

This invention relates to oil-in-water emulsions stabilized by the presence of insoluble protein in the aqueous phase. The compositions are suitable for use as or in wound dressings.

Biopolymers, such as animal proteins and plant polysaccharides, have been used in recent years in a number of diverse applications, including biomedical applications. For example, alginates (which are polysaccharides derived from seaweeds) are valuable for their haemostatic properties, while collagen (the major protein of skin and connective tissue) has been used in wound dressing materials, as well as in surgical sponges (see, for example, U.S. Pat. Nos. 3,632,361; 4,412,947; 3,823,212; Chvapil, J. Biomed. Mater. Res. 11, 721 to 741 (1977); Huc, J. Am. Leather Chem. Assoc. 80, 195 to 212 (1985)1; and GB-A-2058084). Collagen is attractive in a biomedical context, principally because it is biocompatible, resorbable, structurally versatile and also has haemostatic properties.

Japanese laid-open patent application JP-A-55084167 (Lion Hamigaki KK) describes medicated sponge bands for the treatment of periodontal disease. The sponge bands comprise a sponge matrix of a soluble polymer having droplets of non-volatile oil dispersed therein. The non-volatile oil may contain dissolved medicaments. The sponge bands are formed by freeze drying an oil-in-water emulsion having the soluble polymer dissolved in the aqueous phase. The soluble polymers may be natural, synthetic or semi-synthetic polymers such as cellulose derivatives, natural gums, sodium alginate, gelatin or polyvinylpyrrolidone. In use, the medicated sponge bands are applied to affected areas such as mucous membranes in the oral cavity. The bands rapidly absorb water to form a sticky oil-in-water ointment. The sponge band is normally provided with an impermeable backing layer to improve the persistence of the ointment at the affected area.

The present invention is based on the discovery that insoluble proteins such as fibrous collagen are effective emulsifiers. The resulting oil-in-water emulsions having insoluble protein in the aqueous phase are suitable for use as wound contacting materials in wound dressings.

According to the present invention there is provided an oil-in-water emulsion comprising from 1% to 50% by weight of an oil, from 0.5% to 25% by weight of an insoluble protein and from 25% to 98.5% by weight of water.

Preferably, the oil-in-water emulsion comprises from 10% to 35% by weight of the oil. The term "oil" includes all oleaginous materials that are liquid or semisolid at temperatures below 40° C. Preferred oils include mineral oils and vegetable oils such as sesame seed oil, rapeseed oil, sunflower oil, arachis oil, or corn oil.

The consistency of the oil-in-water emulsions ranges from liquid to semi-solid to solid at 25° C., depending on the insoluble protein content. Preferred emulsions contain between 1% and 15% of the insoluble protein. Lower protein content generally results in an emulsion having a semi solid gel or paste-like consistency at 25° C. and therefore useful as a wound dressing ointment. Emulsions containing more than about 5% by weight of the insoluble protein generally have a more solid or waxy consistency and are suitable for use as the wound contacting layer of multilayered wound dressings. Cast or extruded into films these emulsions can themselves be applied directly as wound dressings.

Oil-in-water emulsions according to the present invention may also be characterised by their penetrability. The penetrability is defined by reference to the force in Newtons required to compress or penetrate the emulsion by 10 mm using a cylindrical steel probe 15 mm in diameter at a speed of 130 mm/minute. The force is preferably from 0.1 to 20 Newtons, more preferably from 0.5 to 15 Newtons, and most preferably from 1 to 10 Newtons.

The insoluble protein may be a naturally occurring insoluble protein such as an insoluble fibrous protein. Alternatively, the insoluble protein may be a soluble protein such as gelatin that has been cross-linked to render it insoluble. Suitable cross-linking agents include HMDI (hexamethylene diisocyanate), water soluble carbodiimide or glutaraldehyde. In other embodiments the insoluble protein may in fact be a soluble protein that is present in the aqueous phase at concentrations above its solubility limit. In yet other embodiments the insoluble protein may be precipitated from solution in situ—for example, collagen fibres can be precipitated from collagen solutions by either adding polyethylene glycol at neutral pH as described in U.S. Pat. No. 4,980,403, or by adding salts, or by forming a gel of soluble collagen at 37° C., mechanically disrupting the gel, centrifuging and retaining the resulting fibrous pellet as described in U.S. Pat. No. 4,655,980. All of the above embodiments are included within the scope of the present invention.

Suitable insoluble fibrous proteins preferred for the process of the invention may include the so-called structural fibrous proteins and derivatives thereof, such as insoluble collagen, keratin, fibrin and elastin.

Preferably, the insoluble fibrous protein is predominantly comprised of insoluble collagen, which may suitably be obtained from bovine skin. Such collagen preferably has a fibre length of from 0.005 to 5 mm, and more preferably from 0.01 to 3 mm. Conveniently, but not essentially, the collagen is swollen prior to use, either in acid or in alkali. Acid swelling is preferred, with optimum swelling occurring in the pH range 2 to 3.5. Organic acids (e.g. acetic acid, malic acid, lactic acid and citric acid) and mineral acids (e.g. hydrochloric acid and sulphuric acid) can be used, but organic acids are preferable since they facilitate greater swelling of the collagen.

The oil-in-water emulsions according to the present invention may also contain soluble biopolymers such as soluble proteins or soluble polysaccharides. Preferred soluble proteins include gelatin and pepsin-solubilised collagen. Preferred soluble polysaccharides include sodium alginate and hyaluronic acid. The soluble biopolymer may be present in order to regulate the consistency of the emulsion, for example in the case of gelatin. The soluble biopolymer may assist in emulsifying and stabilising the emulsion, for example in the case of gelatin and pepsin-solubilised collagen. Yet other soluble biopolymers such as alginates and hyaluronic acid derivatives are known to promote wound healing.

It is envisaged that the oil-in-water emulsions according to the present invention will preferably be substantially free from added emulsifiers other than insoluble and soluble biopolymers. However, in some cases it may be advantageous to include added emulsifiers such as the well known commercial emulsifiers including lecithins, mono- and diglycerides of fatty acids and sorbitan esters.

Preferably the oil-in-water emulsions according to the present invention are medicated. That is to say, the emulsions contain pharmaceutically active agents intended to assist wound healing. The emulsions can accommodate both hydrophilic and hydrophobic active agents.

Hydrophobic pharmaceutically active agents, which tend to partition into the oil phase of the emulsion, include steroids and retinol. Hydrophilic pharmaceutically active agents include analgesics, steroids, antibiotics such as penicillins and cephalosporins, antiseptics such as chlorhexidine, beta-blockers such as propanolol, and peptide hormones and growth factors. The hydrophilic active agents tend to partition into the aqueous phase of the emulsion. The rate of release of the hydrophilic active agents is modified by the presence of insoluble protein and droplets of oil in the emulsion and this allows the rate of release to be adjusted for different applications by adjusting the protein and/or the oil content of the emulsion.

The emulsions according to the present invention are particularly useful as ointments or dressings specifically for the treatment of burns. The hydrophobic nature of the material (the degree of hydrophobicity is dependant on the content of the oleaginous phase) may be used to reduce moisture loss from wounds, to reduce trauma on removal, or to deliver active agents to the wound site. In these wound dressings or implants, factors which may promote wound healing can be incorporated into the matrix, these include growth factors, glycosaminoglycans (GAGS) such as hyaluronic acid, chondroitin sulphate or the low molecular weight heparins. Furthermore additional factors which have potential to reduce wound scarring such as mannose-6-phosphate, TGF-$\beta_3$, and anti TGF $\beta_1$ and $\beta_2$ can be dissolved/suspended in either the hydrophobic or hydrophilic phases of these matrices.

The emulsions according to the present invention may also contain anti-oxidants to protect the oil, and other preservatives.

The emulsions according to the present invention can be prepared by homogenising the oil, insoluble protein and water at high shear, to produce microdroplets of the oil dispersed in an aqueous suspension of the insoluble protein. Typically, the droplets have a maximum dimension less than 25 μm, and generally in the range 0.5 μm to 10 μm.

Homogenisation may be carried out by any suitable means, such as by a jet homogeniser, ultrasonic homogeniser or blade/shear homogeniser. The solid or semisolid emulsions may optionally be heated to 60° C. to 80° C. during or after the homogenising step. Depending on the temperature of the emulsions they can be poured, spread or extruded in any desired shape. The compositions set on cooling.

The emulsions can be extruded or poured onto a secondary wound dressing, such as a gauze, or onto a backing layer, such as a film. The resulting layered structure is easier to handle and apply. In the case of heavily exuding wounds, the emulsions according to the present invention may not facilitate the removal of exudate from the wound site. Accordingly, the emulsion films or implants may be perforated during manufacture so as to assist transmission of exudate from the wound site to the secondary dressing.

The emulsions according to the present invention are primarily useful as or in ointments or dressings for the treatment of burns, wounds or periodontal disease. The emulsions are hydrophobic and thereby prevent water loss from the burn or wound. Moreover, the emulsions are non-sticky and do not adhere to the wound tissues making removal non-traumatic. The emulsions are cool and soothing on application, especially if previously refrigerated. The emulsions can provide for controlled release of both hydrophobic and hydrophilic active agents into the wound.

Solid oil-in-water emulsions according to the present invention having higher insoluble protein contents may be used as bioabsorbable wound dressing materials or implants.

The emulsions according to the present invention also have applications in the cosmetic industry. The fluid emulsions can be used as creams, while the semisolid emulsions have applications as emollients and cosmetic bases. Hydrophilic or hydrophobic active agents specifically adapted for skin care can be incorporated in the emulsions.

Embodiments of the oil-in-water emulsion according to the present invention will now be described further, as follows:

EXAMPLE 1

Insoluble Collagen/Oil Emulsion

A. Preparation of Fibrous Collagen from Hide

The insoluble collagen used in the emulsion preparation is preferably collagen which is pre-washed and rendered largely free of fat, non-collageneous proteins, polysaccharides and other carbohydrates as described in U.S. Pat. No. 4,614,794 or U.S. Pat. No. 4,320,201 or British Patent Spec. No. 1 204 438. The collagen is suspended in clean deionised pyrogen free water and homogenised to a fine fibrous suspension by passage through a homogenising system. Suitable homogenising systems are described in U.S. Pat. No. 4,320,201. Homogenising may be continued until a desired degree of fibre division is achieved. This results in a preferred fibre size of between 0.01 and 10 mm. The collagen can then be used in this form (as an aqueous slurry) or freeze dried and milled to form a dehydrated or partially hydrated mass of fibres.

B. Preparation of a Collagen Stabilised Oil-in-water Emulsion having a Fluid Consistency The following components were used to prepare the emulsion:

| Fibrous Collagen | 3.7 g |
|---|---|
| Water | 175 ml |
| Vegetable Oil (Sesame Oil) | 75 g |

The water was chilled to 4° C. and placed in a Waring Blendor. The collagen (prepared as in A) and oil were then added and the mixture was homogenised at high speed for a total of 90 seconds. The resulting fluid emulsion showed excellent stability on standing overnight at 4° C.

EXAMPLE 2

Insoluble Collagen/Oil Emulsion Ointment

An antiseptic ointment consisting of a medicated insoluble collagen based oil-in-water emulsion was prepared from the following ingredients:

| Insoluble Fibrous Collagen | 8.75 g |
|---|---|
| Water | 170 ml |
| Vegetable Oil (Sesame Oil) | 50 g |
| Chlorhexidine gluconate | 3 g |

The water was acidified to pH 4.5 with lactic acid. The acidified water was chilled to 4° C. and placed in a Waring Blendor. The collagen (prepared as in Example 1 above), oil and chlorhexidine gluconate were then added and the mixture was then homogenised at high speed for a total of 90 secs. The resulting emulsion has a semi-solid consistency and shows no tendency to separate into oil and water fractions on prolonged storage at 4° C.

EXAMPLE 3

Solid Oil-in-water Emulsion Stabilised with Insoluble Collagen

The following components were used to form a solid oil-in-water emulsion stabilised with insoluble fibrous collagen:

| | |
|---|---|
| Insoluble Fibrous Collagen | 18.75 g |
| Water | 175 ml |
| Vegetable Oil (arachis oil) | 50 g |

The water was chilled to 4° C. and placed in a Waring Blendor. The collagen and oil were then added and the mixture was homogenised at high speed for a total of 90 secs. The emulsion was then poured into a tray and cooled to 4° C. whereupon it set to a solid consistency.

As an alternative, the emulsion can be extruded in any desired shape at 19° C.±4° C. and 345 kPa and then cooled to 4° C. Preferably the emulsion is extruded as a continuous sheet.

The solid oil-in-water emulsion may be used as a wound dressing material.

The above examples are intended for the purpose of illustration only. Many other embodiments of the present invention as defined in the accompanying claims will be apparent to the skilled reader.

We claim:

1. A method of treating burns or wounds comprising applying to the surface of the burn or wound an effective amount to treat the burn or wound of an oil-in-water emulsion comprising, prior to its application, from 1% to 50% by weight of an oil, from 0.5% to 25% by weight of an insoluble protein and from 25% to 98.5% by weight of water.

2. A method according to claim 1 wherein the oil in the oil in water emulsion is present in an amount of from 10% to 35% by weight.

3. A method according to claim 1 wherein the insoluble protein of the oil in water emulsion is present in an amount of from 1% to 15% by weight.

4. A method according to claim 1 wherein the insoluble protein comprises an insoluble fibrous protein.

5. A method according to claim 4 wherein the insoluble fibrous protein is selected from the group consisting of collagen, keratin, fibrin, elastin, and mixtures thereof.

6. A method according to claim 1 wherein the oil and water emulsion further comprises up to 20% by weight of a soluble biopolymer or biopolymer derivative.

7. A method according to claim 6 wherein the soluble biopolymer or biopolymer derivative is selected from the group consisting of gelatin, pepsin solubilized collagen, alginates, hyaluronic acid and derivatives and mixtures thereof.

8. A method according to claim 1 wherein the oil and water emulsion further comprises a pharmacologically active agent.

9. A method according to claim 8 wherein the pharmacologically active agent is selected from the group consisting of antiseptics, antibiotics, growth factors, hormones, cytokines and peptides.

* * * * *